(12) United States Patent
Ilyin

(10) Patent No.: US 11,497,207 B2
(45) Date of Patent: Nov. 15, 2022

(54) DEVICE FOR PRESERVING BLOOD PRODUCTS AND CELLULAR CULTURES IN A GAS MEDIUM UNDER PRESSURE

(71) Applicant: Rich Technologies Holding Company, LLC, Buffalo, NY (US)

(72) Inventor: Ilya Ilyin, Wayland, MA (US)

(73) Assignee: Rich Technologies Holding Company, LLC, Buffalo, NY (US)

( * ) Notice: Subject to any disclaimer, the term of this patent is extended or adjusted under 35 U.S.C. 154(b) by 392 days.

(21) Appl. No.: 15/884,676

(22) Filed: Jan. 31, 2018

(65) Prior Publication Data

US 2018/0249703 A1    Sep. 6, 2018

Related U.S. Application Data

(60) Provisional application No. 62/466,702, filed on Mar. 3, 2017.

(51) Int. Cl.
*A61M 1/02* (2006.01)
*A01N 1/02* (2006.01)

(52) U.S. Cl.
CPC ......... *A01N 1/0242* (2013.01); *A01N 1/0252* (2013.01); *A01N 1/0289* (2013.01);
(Continued)

(58) Field of Classification Search
CPC ............................ A61M 1/209; A61M 1/0286
See application file for complete search history.

(56) References Cited

U.S. PATENT DOCUMENTS 3,901,083 A    8/1975 Wallace
4,056,260 A    11/1977 David
(Continued)

FOREIGN PATENT DOCUMENTS

CN    105163704 A    12/2015
EP    1541113 A1    6/2005
(Continued)

OTHER PUBLICATIONS

U.S. Searching Authority, International Search Report and Written Opinion for corresponding PCT Application No. PCT/US2018/01611 (dated Apr. 12, 2018.
(Continued)

*Primary Examiner* — Donald R Spamer
(74) *Attorney, Agent, or Firm* — Michael Best & Friedrich LLP

(57) ABSTRACT

A device that can be used to store blood product and/or cellular culture that may or may not be under pressure. The device includes a chamber that can be hermetically sealed and a flexible secondary bag which can be placed in the chamber. The chamber is designed to receive at least one secondary bag that contains a conventional storage bag containing blood product and/or cellular culture. The storage conditions are created in the chamber and may or may not include 1) creating a pressure higher than atmospheric pressure, 2) creating a refrigerated temperature, and/or 3) providing agitation to the secondary bag. The secondary bag is filled with a gas system that is used to facilitate in the storage of the blood product and/or cellular culture. The secondary bag can be made of a material and/or include a coating or film that is impermeable to the gas system and to the gas inside the chamber. The higher-than-atmospheric pressure inside the chamber can be created by pumping an inexpensive gas, for example, air, into the chamber. The gas used to pressurize the chamber can be different from the gas system in the secondary bag.

35 Claims, 7 Drawing Sheets

(52) U.S. Cl.
CPC .......... *A61M 1/025* (2013.01); *A61M 1/0272* (2013.01); *A61M 2202/0291* (2013.01); *A61M 2202/0427* (2013.01)

(56) References Cited

U.S. PATENT DOCUMENTS

| | | | |
|---|---|---|---|
| 4,079,729 | A | 3/1978 | Cornell |
| 4,135,509 | A | 1/1979 | Shannon |
| 4,338,933 | A | 7/1982 | Bayard et al. |
| D267,040 | S | 11/1982 | David |
| 4,568,345 | A | 2/1986 | Keilman et al. |
| 5,158,533 | A | 10/1992 | Strauss et al. |
| 5,269,924 | A | 12/1993 | Rochat |
| 5,433,716 | A | 7/1995 | Leopardi et al. |
| 5,477,704 | A * | 12/1995 | Wright .................... B04B 15/02 62/381 |
| 5,566,713 | A | 10/1996 | Lhomer et al. |
| 5,644,930 | A | 7/1997 | Albertson et al. |
| 5,919,622 | A | 7/1999 | Macho et al. |
| 7,638,100 | B2 | 12/2009 | Dawes |
| 2006/0030821 | A1 | 2/2006 | Lee et al. |
| 2007/0219524 | A1 | 9/2007 | Burnouf et al. |
| 2007/0221532 | A1 | 9/2007 | Diliberto |
| 2008/0009061 | A1 | 1/2008 | Goto et al. |
| 2008/0307821 | A1 * | 12/2008 | Zenobi .................... A61M 1/02 62/331 |
| 2008/0311007 | A1 | 12/2008 | Helmerson |
| 2009/0012493 | A1 | 1/2009 | Harig |
| 2010/0009334 | A1 | 1/2010 | Ilyin et al. |
| 2012/0115124 | A1 | 5/2012 | Yoshida et al. |
| 2012/0175319 | A1 | 7/2012 | Cotton et al. |
| 2013/0157249 | A1 | 6/2013 | Ilyin et al. |
| 2014/0031976 | A1 | 1/2014 | Reinhardt et al. |
| 2014/0144800 | A1 | 5/2014 | Delorme et al. |
| 2014/0158604 | A1 * | 6/2014 | Chammas ........... A61M 1/3616 210/256 |
| 2014/0202908 | A1 | 7/2014 | Liburd et al. |
| 2014/0227678 | A1 * | 8/2014 | Ilyin ...................... A01N 1/021 435/2 |
| 2015/0305324 | A1 * | 10/2015 | Ilyin .................... A61M 1/0277 435/2 |
| 2016/0082043 | A1 * | 3/2016 | Khan .................... A61K 9/1617 604/410 |
| 2016/0095309 | A1 | 4/2016 | Reuteler |

FOREIGN PATENT DOCUMENTS

| | | |
|---|---|---|
| WO | 2012125955 A2 | 9/2012 |
| WO | 2012177820 A1 | 12/2012 |
| WO | 2013049118 A1 | 4/2013 |
| WO | 2014134503 A1 | 9/2014 |
| WO | 2016172645 A1 | 10/2016 |

OTHER PUBLICATIONS

The University of Arizona, "Index of /students/courselinks/spring08/atmo336s1/courses/fall08/nats101s3/lecture_notes," <http://www.atmo.arizona.edu/students/courselinks/spring08/atmo336s1/courses/fall08/nats101s3/lecture_notes/>, p. 2, accessed Jun. 13, 2016.
The University of Arizona, "Lecture Notes from Department of Atmospheric Sciences," dated Thursday Sep. 18, 2008 <http://www.atmo.arizona.edu/students/courselinks/spring08/atmo336s1/courses/fall08/nats101s3/lecture_notes/sep18.html>, accessed Jan. 26, 2016.
International Search Report and Written Opinion for Application No. PCT/US2012/043449 dated Sep. 21, 2012 (7 pages).
Canadian Patent Office Examination Report for Application No. 2,835,075 dated Apr. 29, 2020 (3 pages).
Russian Patent Office Action and Search Report for Application No. 2019130972 dated Apr. 16, 2020 (24 pages, English translation included).
First Office Action issued from the Chinese Patent Office for related Application No. 2018800251595 dated Sep. 8, 2021 (12 Pages with partial English translation).
Supplementary Search Report issued from the European Patent Office for related Application No. 18761388.0 dated Jan. 12, 2021 (12 Pages).
Office Action issued from the Russian Patent Office for related Application No. 2019130972.04 dated Feb. 26, 2021 (9 Pages including English Translation).
English Translation of First Substantive Office Action issued from the Israel Patent Office for related Application No. 268991 dated May 18, 2021 (5 Pages).
Russian Patent Office Action and Search Report for Application No. 2019130972 dated Jul. 20, 2021 (15 pages, English translation included).
Reddoch et al., Hemostatic Function of Apheresis Platelets Stored at 4° C. and 22° C., Shock, vol. 41 Supplement 1, 2014, pp. 54-61.
Notification of Reasons for Refusal for related Application No. 2019-547643 dated Dec. 1, 2021 (19 Pages including English Translation).

* cited by examiner

DEVICE FOR PRESERVING BLOOD PRODUCTS AND CELLULAR CULTURES IN A GAS MEDIUM UNDER PRESSURE

The present invention claims priority on U.S. Provisional Application Ser. No. 62/466,702 filed Mar. 3, 2017, which is incorporated herein by reference.

The present invention refers to the field of medicine, and in particular to a method and device to the preserve of blood products and cellular cultures.

BACKGROUND OF THE INVENTION

One known method for preserving platelets is described in U.S. Pat. No. 8,158,339, which is incorporated herein by reference. This method involves the preparation of platelet plasma out of the whole donated blood, keeping the platelet plasma in a gas medium containing from 65-100 vol. % of xenon under pressure from approximately 3.5-5 bars, subsequently cooling the platelet plasma down to a temperature of approximately 3-6° C., and storing the platelet plasma under the conditions of the above-indicated temperature and pressure of gas medium. The '339 patent discloses that the method is implemented by placing the platelet concentrate in a gas-impermeable container into which a xenon-containing gas medium is fed under pressure, or using conventional gas-permeable bags intended for storing biological fluids (in particular, blood and blood components) and placing them in a gas-impermeable container into which a xenon-containing gas medium is fed under pressure. This method provides storage of platelets during a period of at least one week, which may not be long enough for some applications. Secondly, this method is best performed on small volumes of platelet concentrate, of the order of units of ml (i.e., placed into a vial, for example). It is believed that a sufficient amount of oxygen (required for maintaining metabolic processes in plasma) stays in a vial partially filled with such volume of platelet plasma. However, in actual practice, the platelets are required to be stored in standard bags with a volume of at least 200 ml, not in small vials. When the platelets are stored in bags, the amount of oxygen available for the platelets may be insufficient for aerobic respiration, which can limit the duration of platelet plasma storage. For the implementation of this method, it is proposed to use conventional gas-impermeable containers intended for storing biological fluids, in particular, blood and blood components.

Usually such bags for containing blood and blood components are manufactured by sealing two flat blanks along the perimeter, which ensures high manufacturability of production process and low cost of bags. When using such a bag in a conventional way, the fluid contained in the bag exerts pressure upon the sealed joint by the weight of the fluid. The pressure of the gas medium inside the bag generally does not exceed atmospheric pressure. As such, this bag manufacturing process ensures high reliability of bags in the case of ordinary use.

However, when implementing the method for preserving blood and blood components as described in the '339 patent, which involves keeping and storing biological material in a gas medium under pressure that can exceed atmospheric pressure by 3.5-5 times, the use of such conventional bags is limited by the strength of the sealed joint. Taking into account the character of the load on the sealed joint due to bag inflation by the gas pressure in the bag, the sealed joint strength should be considerable to avoid the rupture of the bag. The adequate strength of the seal of the bag could be obtained, for instance, by increasing the bag material thickness, by selecting such a material that produces a monolith seam after sealing, or by additional reinforcement of the bag. Such bag modifications, however, can limit the ability of the bag to change shape when gas is pumped into the bag. Also, all such measures to increase the strength of the bag seam will make the bag more expensive, which is highly undesirable because such bags are single-use products.

A method and device for preserving blood or its components in a gas medium under pressure and system for the same is also described in WO 2012/177820, which is incorporated herein by reference. According to the '820 publication, the blood or blood components are placed in a bag that is made of a xenon gas-permeable material. The bag is then placed into a hermetically-sealed cylindrical chamber into which xenon-containing gas (with a xenon content of at least 65 vol. %) is fed under pressure until the pressure in the chamber reaches the approximate of 3.5 to 5 bars, after which the chamber is placed in storage at a temperature within the range from 3-6° C. Bags that are made of the gas-permeable material are designed to allow xenon to pass through the bag for the implementation of this method. In this method, the xenon-containing gas (fed under pressure into the chamber) passes through the bag wall, after which the blood or blood components in the bag are partially or fully saturated with xenon. According to this method, the bag with the blood or blood components is placed in a cylindrical chamber and, during storage, the chamber is positioned vertically. The bag in the chamber is also positioned vertically, and the blood or blood components are not stirred in the course of storage. Xenon (contained in the gas fed into the chamber) passes through the bag wall and the blood product in the bag is saturated with xenon, which ensures preservation of the blood product. The absence of the stirring and vertical positioning of the bag in the course of storage can lead to the platelets settling on a small area of bag bottom, thus forming a dense deposit by the end of the storage period. Platelets in such a deposit change their properties and considerable number of platelets are activated and stick together. These platelets produce micro-aggregates, which result in the reduction in the number of free platelets, which, in turn, leads to a decrease in platelet concentrate efficiency. Moreover, platelets that are stuck together can lead to the formation of aggregates of considerable size, which are dangerous for the recipient because after transfusion they are capable of clotting the blood vessels, thus leading to disturbed blood circulation. With regard to the bag storage chamber, movement of the chamber can be cumbersome between users, for example, between a blood bank facility and a hospital.

The rigid container disclosed in '820 publication is strong enough to maintain a gas pressure inside the chamber that is higher than atmospheric pressure, and thus requires significant amount of gas to be pumped into the container in order to create such high pressures. If the container is similar in shape to the bag with blood product stored inside, it becomes difficult to place the bag into and out of the container. If the rigid container has an opening large enough to easily place the bag inside, it becomes difficult to hermetically seal such an opening. If the gas that is to be inserted into the chamber is expensive and its use needs to be minimized to reduce the cost of storage, such approach may become cost prohibitive.

In view of the current state of the art, there remains a need for a device which provides storage conditions for preserving blood products and cellular cultures in a gas medium under pressure that is reliable, inexpensive, and easy to use in the blood bank and hospital environment.

SUMMARY OF THE INVENTION

The present invention is directed to an improved device for preserving blood products and live cellular cultures that can be used to store blood product or live cellular culture in which the blood product or live cellular culture may or may not be under pressure. The device is configured to provide storage conditions for preserving blood products and live cellular cultures in a gas medium under pressure that is reliable, inexpensive and easy to use in a blood bank, hospital environment, etc. For the blood product, the stored blood product is typically used for later transfusion into a living creature (e.g., human, animal, etc.). For the live cellular cultures, the live cellular cultures can also be used for later transfusion into a living creature or be used in transplants, vaccinations, oral applications, nasal application, skin patches, etc.

In one non-limiting aspect of the present invention, there is provided a device for preserving blood products (e.g., red blood cells, platelets, plasma, cryoprecipitate, albumin, coagulation factors, immunoglobulins, etc.) and/or cellular cultures in a gas medium under a pressure that is greater than at atmospheric pressure (e.g., 1 atm.). The device for preserving blood products and/or cellular cultures includes a chamber that can be hermetically sealed and which can receive one or more receptacles (e.g., barrier film bag, flexible barrier film bag) that contain blood products and/or cellular cultures. The receptacle containing the blood products and/or cellular cultures is generally filled with a gas prior to the receptacles being inserted into the chamber of the device; however, this is not required. The higher-than-atmospheric pressure inside the chamber can be created by pumping a gas into the chamber once the chamber is sealed. An inexpensive gas, for example, air can be pumped into the chamber; however, other or additional gasses can be pumped into the chamber. The increased pressure in the chamber is used to create a desired pressure of the gas in the receptacle. Generally, the receptacle is not permeable to the gas that is pumped into the chamber.

In another and/or alternative non-limiting aspect of the invention, the chamber of the device can be hermetically sealed and filled with gas in order to a create pressure inside that exceeds atmospheric pressure. The chamber (e.g., hermetically-sealed chamber) can optionally include an inlet channel that fluidly connects the cavity of the chamber to a pump (e.g. compressor pump) or pressurized gas source (e.g., gas cylinder, gas cylinder with a regulator, etc.), which can be used to supply gas (e.g., air, nitrogen, noble gas, inert gas, etc.) into the chamber at pressure which exceeds atmospheric pressure. The chamber optionally can include an outlet channel that connects the cavity and the exterior of the chamber, and which is designed to release the gas to the exterior atmosphere of the chamber and to reduce the pressure in the chamber (e.g., reduce pressure in chamber to atmospheric pressure, etc.). In one non-limiting configuration, the same inlet channel can be used to feed gas into and/or remove gas from the cavity of the chamber; however, this is not required. As can be appreciated, the inlet channel and/or optional separate outlet channel can optionally include a one-way valve.

In another and/or alternative non-limiting aspect of the invention, the chamber can optionally contain one or more shelves or racks to accommodate a plurality of receptacles. The specific geometric configuration of the rack can be designed to maximize use of the space inside the chamber and to be able to maximize the number of receptacles which can be placed in the chamber; however, this is not required.

The one or more racks or shelves inside the chamber can optionally be connected to a rotation device that provides rotational motion to the one or more racks or shelves in the chamber while one or more receptacles are positioned on the one or more racks or shelves. The type and configuration of the rotation device is non-limiting. The rotation device can be located fully inside the chamber and/or be partially located externally to the chamber. The rotation generated by the optional rotation device can be used to agitate blood product in the receptacle to keep the cells suspended at all times during storage. In an alternative non-limiting embodiment of the invention, the chamber alternatively or also can optionally rotate to provide the necessary agitation to the blood product and/or cellular cultures in the chamber; however, this is not required. The rotation of the chamber and/or the one or more racks or shelves inside the chamber is typically about the longest axis of the receptacle so as to minimize the shakes applied to the blood product and/or cellular culture in the receptacle during the agitation of the blood product and/or cellular culture in the receptacle. The speed of rotation is generally selected so as to also minimize the shakes applied to the blood product and/or cellular culture in the receptacle during the agitation of the blood product and/or cellular culture in the receptacle, but sufficient speed to keep the blood product and/or cellular culture in the receptacle suspended in the liquid in the receptacle at all or substantially all times during storage. The rotation of the chamber and/or the one or more racks or shelves inside the chamber can be continuous during the time of storage of the one or more receptacles in the chamber, or can be intermittent. The speed and time of rotation is selected to keep the blood product and/or cellular culture in the receptacle suspended in the receptacle at all or substantially all times during storage. The operation and speed of the rotation device can be manual and/or controlled by a rotation control system.

In another and/or alternative non-limiting aspect of the invention, the chamber can optionally be equipped with a cooler and/or a thermostat. The cooling system (when used) can be configured to cool the chamber and to provide a refrigerated temperature (0-15° C.). The cooling system can optionally be configured to have a temperature control system that allows a temperature to be set or preset.

In another and/or alternative non-limiting aspect of the invention, the receptacle includes a conventional storage bag that contains blood product and/or cellular culture and a secondary bag. The secondary bag can optionally be flexible and is generally formed of a material and/or includes a barrier film which is impermeable to one or more gasses that are inserted into the chamber. In one non-limiting arrangement, the secondary bag is formed of a material and/or includes a barrier film which is impermeable that inhibits or prevents gases from passing though the secondary bag. In one non-limiting embodiment of the invention, the secondary bag is impermeable to xenon gas. In another non-limiting embodiment of the invention, the secondary bag is impermeable to oxygen and xenon. In another non-limiting embodiment of the invention, the secondary bag is impermeable to xenon and the gas components of air (e.g., oxygen, nitrogen, carbon dioxide).

In another and/or alternative non-limiting aspect of the invention, the secondary bag includes a valve or inlet for connection with a gas supply line so that a gas can be inserted into the secondary bag after the secondary bag has been sealed. The valve or inlet can be located at any region on the secondary bag (e.g., on the side of the secondary bag, at one of the end of the secondary bag, etc.). In one non-limiting embodiment of the invention, the valve is made of a flexible sleeve attached to the one end of the secondary bag in such a way that the valve at least partially extends inside the secondary bag. The outlet of the gas supply line can be partially inserted in the sleeve or releasable connected to the sleeve of the valve. When gas is supplied under pressure, the sleeve of the valve can be configured to allow the gas to freely flow into the cavity of the secondary bag. When the gas supply line is closed, the internal excessive pressure in the secondary bag can be configured to collapse the sleeve and keeps the gas inside the secondary bag. As can be appreciated, many other arrangements can be used. Alternatively, a one-way valve can optionally be installed on/included in the fitting which can be used to allow the insertion of the gas into the secondary bag and, on the other hand, prevent gas egress from the secondary bag. The other end of the secondary bag can be initially configured to be open and then be subsequently sealed by heat sealer, adhesive and/or contain a closure mechanism; however, this is not required.

In another and/or alternative non-limiting aspect of the invention, the secondary bag is configured so that it can partially or fully contain a conventional storage bag of blood product and/or cellular culture. For instance, the secondary bag can be designed such that a conventional storage bag that contains blood product and/or cellular culture is inserted into the cavity of the secondary bag and then the secondary bag can thereafter be sealed with the conventional storage bag inside the cavity of the secondary bag. As can be appreciated, the secondary bag can be designed to fully contain other types of conventional storage bags (e.g., conventional storage bag of platelets, conventional storage bag of plasma, conventional storage bag of blood, etc.), and/or be designed to contain more than one conventional storage bags. Generally, the secondary bag is formed of a different material than the conventional storage bag of blood product and/or cellular culture, and/or the secondary bag includes one or more coatings that are not included on the conventional storage bag of blood product and/or cellular culture; however, this is not required. The thickness of the secondary bag can be the same as or different from the conventional storage bag of blood product and/or cellular culture. Generally, the secondary bag is less permeable to one or more gasses than the conventional storage bag of blood product and/or cellular culture; however, this is not required. Generally, the secondary bag is designed to be able to be subjected to higher pressures in the sealed cavity of the secondary bag before gas leakage or rupture of the secondary bag occurs as compared to the sealed cavity of the conventional storage bag; however, this is not required.

In another and/or alternative non-limiting aspect of the invention, there is provided a blood product preservation method which includes one or more steps of blood product and/or cellular culture packaging, one or more steps of treating the packaged blood product and/or cellular culture with a gas system, one or more steps of storing the treated blood product and/or cellular culture, and one or more steps of preparing the stored blood product and/or cellular culture for use in an human, animal or other living organism. In accordance with one non-limiting method of the present invention, the blood product and/or cellular culture is placed in a hermetically-sealed storage bag. Such storage bag can be a conventional storage bag that is used to store blood product and/or cellular culture. For blood products, one such conventional storage bag is a blood transfusion bag. The conventional storage bag is generally made of a material that is permeable to xenon or xenon and oxygen. The conventional storage bag that contains the blood product and/or cellular culture is then placed in a secondary bag and then hermetically sealed in the secondary bag. The secondary bag is generally made of a material and/or includes a barrier film or coating that prevents one or more gasses (e.g., xenon, oxygen, nitrogen, carbon dioxide, etc.) from passing through the material and/or barrier film or coating on the secondary bag. After the conventional storage bag is hermetically sealed in the secondary bag, a gas system that is to be used to preserve the blood product and/or cellular culture that is contained in the conventional storage bag is inserted into the secondary bag. The material of the conventional storage bag is designed to be permeable to the gas system, and the secondary bag is designed to be not permeable to the gas system. As such, once the gas system is inserted into the secondary bag, the gas system cannot escape the secondary bag until the gas system is released from the secondary bag via a valve, etc. or after the secondary bag is cut or punctured. Once the gas system is inserted into the secondary bag, the gas system permeates the conventional storage bag that is located in the hermetically-sealed secondary bag and then partially or fully saturates the blood product and/or cellular culture in the conventional storage bag. The gas system can include one or more gasses. Generally, the gas system contains xenon in an amount that is greater than the natural content of xenon in Earth's atmosphere at sea level and at 20-22° C. When the gas system is supplied into the hermetically-sealed secondary bag, the gas system is generally supplied into the secondary bag in such a way that the gas system is supplied in the cavity of the secondary bag and not directly into the conventional storage bag that is located in the hermetically-sealed secondary bag. As such, the gas system is required to diffuse through the conventional storage bag and mix with the blood product and/or cellular culture in the conventional storage bag. Generally, the pressure of the gas system in the secondary bag is from 0.0001-10 atm. (and all values and rangers therebetween) above the ambient pressure about the secondary bag (e.g., atmospheric pressure (1 atm.)).

In another and/or alternative non-limiting aspect of the invention, the gas system generally has a content of xenon that is greater than the xenon content in the air of Earth's atmosphere at sea level and at 20-22° C. In one non-limiting embodiment of the invention, the xenon content of the gas system is at least 5 vol. %. In another non-limiting embodiment of the invention, the xenon content of the gas system is up to 99.99999 vol. %. In another non-limiting embodiment of the invention, the xenon content of the gas system is at least 5 vol. % and up to about 99.99999 vol. % (e.g., 5 vol. %, 5.00001 vol. %, 5.00002 vol. % . . . 99.99998 vol. %, 99.99999 vol. %) and any value or range there between. In another non-limiting embodiment of the invention, the xenon content of the gas system is from about 50-99.999 vol. %. In another non-limiting embodiment of the invention, the xenon content of the gas system is from about 55-99 vol. %. In another non-limiting embodiment of the invention, the xenon content of the gas system is from about 60-98 vol. %. In another non-limiting embodiment of the invention, the xenon content of the gas system is from about 70-97 vol. %. In another non-limiting embodiment of the invention, the xenon content of the gas system is from about 79-95 vol. %. In another non-limiting embodiment of the invention, the oxygen content of the gas system is about 0-50 vol. % (e.g., 0 vol. %, 0.0001 vol. %, 0.0002 vol. % . . . 49.9998 vol. %, 49.9999 vol. %, 50 vol. %) and any value or range there between. In another non-limiting embodiment of the invention, the oxygen content of the gas system is about 0.1-45 vol. %. In another non-limiting embodiment of the invention, the oxygen content of the gas system is about 2-40 vol. %. In another non-limiting embodiment of the invention, the oxygen content of the gas system is about 3-30 vol. %. In another non-limiting embodiment of the invention, the oxygen content of the gas system is about 5-21 vol. %. In another non-limiting embodiment of the invention, the gas system includes 0-5% by volume (e.g., 0%, 0.0001%, 0.0002% . . . 4.9998%, 4.9999%, 5%) and any value or range therebetween of a gas that is other than xenon or oxygen (e.g., carbon dioxide, noble gas, nitrogen). In another non-limiting embodiment, the gas system of xenon, $CO_2$ and optionally containing nitrogen. In one non-limiting formulation, the gas system includes at least 9 vol. % xenon (e.g., 9-99 vol. %), at least 1 vol. % $CO_2$ (e.g., 1-10 vol. %) and optionally $N_2$ (e.g., 0-90 vol. %). In another non-limiting formulation, the gas system includes at least 95 vol. % xenon (e.g., 9-99 vol. %), at least 1 vol. % nitrogen and/or $CO_2$. In one non-limiting mixture, the xenon volume percent is greater than the volume percent of $CO_2$, and the nitrogen volume content, when included, can be greater than or less than the volume content $CO_2$.

In another and/or alternative one non-limiting aspect of the invention, the receptacle that includes a conventional storage bag that contains blood product and/or cellular culture that is positioned in the cavity of a hermetically-sealed secondary bag is placed into the chamber and the chamber is hermetically sealed. Prior to inserting one or more receptacles into the chamber and then hermetically sealing the chamber, a gas system that is to be used to preserve the blood product and/or cellular culture is typically inserted into the cavity of the hermetically-sealed secondary bag that contains the conventional storage bag. The sealing of the chamber can be accomplished by merely closing the door or cover of the chamber and fixating it with high pressure fasteners. As can be appreciate, other or alternative arrangements can be used to hermetically seal the chamber.

In another and/or alternative non-limiting aspect of the invention, after the chamber is hermetically sealed with one or more receptacles in the chamber, the pressure inside the chamber is elevated to pressure higher than ambient pressure (e.g., 1 atm. at sea level, etc.). As defined herein, ambient pressure is the pressure in the sealed cavity of the chamber after the sealing of the chamber, but prior to the adding of gas into the sealed chamber. As such, if the open chamber is located at sea level, the ambient pressure in the cavity of the chamber prior to the sealing of the chamber would be about 1 atm. The increase in pressure in the sealed chamber can be accomplished by filling the chamber with a gas (e.g., air, etc.) through an inlet channel in the chamber. Generally, the gas that is added to the chamber is different from the gas system in the cavity of the secondary bag; however, this is not required. Generally, the secondary bag is not permeable to the gas that is added into the sealed chamber. In one non-limiting arrangement, the inlet channel in the chamber is connected to a compressor wherein the compressor pumps outside air into the cavity of the chamber to cause a pressure increase in the cavity of the chamber. The gas that is fed under pressure into the cavity of the chamber is generally at a pressure that is greater than ambient pressure. In another non-limiting embodiment of the invention, the air is fed under pressure at a pressure that is 0.01-20 bars (e.g., 0.01 bar, 0.02 bars, 1.02 bars . . . 19.98 bars, 19.99 bars, 20 bars, and any value or range therebetween) greater than ambient pressure. In another non-limiting embodiment of the invention, the air is fed under pressure at a pressure that is about 0.1-15 bars greater than ambient pressure. In another non-limiting embodiment of the invention, the air is fed under pressure at a pressure that is about 1.5-10 bars greater than ambient pressure. In another non-limiting embodiment of the invention, the air is fed under pressure at a pressure that is about 2-8 bars greater than ambient pressure. In another non-limiting embodiment of the invention, the air is fed under pressure at a pressure that is about 3.5-5 bars greater than ambient pressure. When the secondary bag is formed of a flexible material, the pressure of the gas system inside the sealed cavity of the secondary bag equilibrates with the pressure inside the sealed chamber. As the gas system equilibrates with the pressure inside the sealed chamber, some of the gas system is caused to diffuse and/or penetrate through the wall of the conventional storage bag that is located in the hermetically-sealed secondary bag, thereby resulting in the partial or full saturation of the blood product and/or cellular culture with gas system.

In another and/or alternative non-limiting aspect of the invention, during the time period that gas is added to the seal chamber or shortly after the gas has been added to the sealed chamber (e.g., 0.001-20 minutes, and all values and ranges therebetween), the one or more receptacles in the sealed chamber are cooled down to a temperature below about 15° C. and above the freezing point of the blood product and/or cellular culture in the receptacle. Generally, the one or more receptacles are inserted into the cavity of the chamber prior to the sealing of the chamber when the ambient temperature is above 15° C.; however, this is not required. For example, the one or more receptacles can be inserted into the cavity of the chamber at room temperature (e.g., 20-25° C.). In one non-limiting embodiment, the sealed chamber is cooled to a temperature of 0-14.99° C. and any value or range therebetween (e.g., 0° C., 0.01° C., 0.02° C., 0.03° C. . . . 14.97° C., 14.98° C., 14.99° C.). In another non-limiting embodiment, the sealed chamber is cooled to a temperature of 0.01-15° C. In another non-limiting embodiment, the sealed chamber is cooled to a temperature of 1-10° C. In another non-limiting embodiment, the sealed chamber is cooled to a temperature of 3° C. to 6° C.

In another and/or alternative non-limiting aspect of the invention, the receptacle or the conventional storage bag that is located in the hermetically-sealed secondary bag is optionally placed in a generally horizontal position (with flat side down) when located in the sealed chamber. For purposes of the present invention, the horizontal position is defined as the longitudinal axis of the conventional storage bag positioned horizontal to a ground surface (e.g., earth surface).

In another and/or alternative non-limiting aspect of the invention, the receptacle while located in the sealed chamber is continuously or periodically agitated so as to inhibit or present the clumping together of cells, platelets, etc. in the conventional storage bag during the storage of the receptacle in the sealed chamber. In one non-limiting embodiment, the receptacle in the sealed chamber, or the sealed chamber itself can be continuously or periodically rotated to cause agitation of the blood product and/or cellular culture in the conventional storage bag.

In another and/or alternative non-limiting aspect of the invention, prior to removing the one or more receptacles from the sealed chamber, some or all of the excess pressure (e.g., pressure above the current pressure external to the chamber) in the sealed chamber is generally released prior to the opening of the sealed chamber. After the sealed chamber is opened, one or more receptacles in the chamber can then be removed from the chamber. Thereafter, the secondary bag is generally opened so as to remove the conventional storage bag from the cavity of the secondary bag. Prior to using the preserved blood product and/or cellular culture after storage, the conventional storage bag can be allowed to warm to room temperature. In one non-limiting embodiment, the warm-up period is about 0.001-20 hours and any value or range therebetween. During the warm-up period, the conventional storage bag is generally exposed to room temperature to allow the conventional storage bag to naturally warm up. Generally, the preserved blood product and/or cellular culture is not used in a human, animal, or other living organism until the preserved blood product and/or cellular culture is warmed up to about 12-35° C. and any value or range therebetween; however, this is not required. Prior to using the preserved blood product and/or cellular culture after the storage, the contents of the conventional storage bag can optionally be stirred (e.g., placing the conventional storage bag on a shaker, hand shaking the conventional storage bag, etc.).

It is one non-limiting object of the invention to provide an improved device for preserving blood product and/or cellular culture wherein the device forms an all-purpose, reliable, easy-to-manufacture and/or easy-to-use device that can be used in the preservation of blood product and/or cellular culture.

It is another and/or alternative non-limiting object of the invention to provide an improved device for preserving blood product and/or cellular culture that includes at least two components, namely a chamber that can be hermetically sealed and receptacle that is designed to fit in the chamber, and which receptacle contains the blood product and/or cellular culture that is to be stored and preserved for later use in a human, animal or other living organism.

It is another and/or alternative non-limiting object of the invention to provide an improved device for preserving blood product and/or cellular culture wherein the cavity in the chamber is designed to fully accommodate a receptacle, wherein the receptacle includes a secondary bag and a conventional storage bag that contains the blood product and/or cellular culture, and wherein the secondary bag includes a cavity that is designed to receive the conventional storage bag so that the conventional storage bag can be sealed in the secondary bag.

It is another and/or alternative non-limiting object of the invention to provide an improved device for preserving blood product and/or cellular culture wherein the chamber can include an inlet channel that fluidly connects the cavity of the chamber to the exterior of the chamber, and which inlet channel can be used to feed gas into and/or remove gas from the cavity of the chamber.

It is another and/or alternative non-limiting object of the invention to provide an improved device for preserving blood product and/or cellular culture wherein the chamber and the receptacle perform different functions, wherein the chamber is designed to withstand large forces and, therefore, prevent significant deformation and damage to the chamber during the introduction, maintainance and removal of pressurized air in the chamber, and wherein the receptacle includes a secondary bag and a conventional storage bag such that the secondary bag prevents gas from entering or leaving the cavity of the secondary bag when the secondary bag is sealed with the conventional storage bag in the cavity of the secondary bag, and wherein a gas system in the sealed cavity of the secondary bag diffuses or penetrates into the conventional storage bag to partially or fully saturate the blood product and/or cellular culture with the gas system in the conventional storage bag.

It is another and/or alternative non-limiting object of the invention to provide an improved device for preserving blood product and/or cellular culture wherein the chamber is designed to be a reusable unit and the receptacle is designed to be disposable after use.

It is another and/or alternative non-limiting object of the invention to provide an improved device for preserving blood product and/or cellular culture wherein the chamber can include one or more racks or shelves to accommodate one or more receptacles.

It is another and/or alternative non-limiting object of the invention to provide an improved device for preserving blood product and/or cellular culture wherein one or more racks or shelves inside the chamber are connected to the agitation arrangement to agitate the blood product and/or cellular culture during storage.

It is another and/or alternative non-limiting object of the invention to provide an improved device for preserving blood product and/or cellular culture wherein the one or more racks or shelves inside the chamber are connected to an agitation arrangement that includes an agitator motor and an axle which protrudes through chamber wall via an airtight bearing mechanism, and which axle engages one or more racks or shelves inside the chamber to cause the one or more racks or shelves inside the chamber to rotate and/or vibrate.

It is another and/or alternative non-limiting object of the invention to provide an improved device for preserving blood product and/or cellular culture wherein the chamber is connected to an agitation arrangement that includes an agitator motor to cause the chamber to rotate and/or vibrate.

It is another and/or alternative non-limiting object of the invention to provide an improved device for preserving blood product and/or cellular culture wherein the chamber can include a refrigeration unit.

It is another and/or alternative non-limiting object of the invention to provide an improved device for preserving blood product and/or cellular culture wherein the chamber is thermally insulated from the outside atmosphere.

It is another and/or alternative non-limiting object of the invention to provide an improved device for preserving blood product and/or cellular culture wherein the chamber includes a temperature sensor to control the refrigeration unit to maintain the temperature inside the chamber.

It is another and/or alternative non-limiting object of the invention to provide an improved device for preserving blood product and/or cellular culture wherein the chamber can include a gas compressor to pump one or more gasses (e.g., air, etc.) into the chamber and to create a pressure that is higher than atmospheric pressure inside the chamber.

It is another and/or alternative non-limiting object of the invention to provide an improved device for preserving blood product and/or cellular culture wherein the chamber is provided by a fitting for fluid communication between the outlet of the compressor and the chamber.

It is another and/or alternative non-limiting object of the invention to provide an improved device for preserving blood product and/or cellular culture wherein the chamber includes a pressure sensor to control the air compressor and to maintain the pressure inside the chamber by switching on and off the air compressor.

It is another and/or alternative non-limiting object of the invention to provide an improved device for preserving blood product and/or cellular culture wherein the chamber can include a drainage or release valve.

It is another and/or alternative non-limiting object of the invention to provide an improved device for preserving blood product and/or cellular culture wherein the chamber can include end fittings to be used to form a fluid connection with another device for preserving blood product and/or cellular culture.

It is another and/or alternative non-limiting object of the invention to provide an improved device for preserving blood product and/or cellular culture wherein a plurality of devices can be stacked together and/or fluidly connected together.

It is another and/or alternative non-limiting object of the invention to provide a method for improved blood product and/or cellular culture storage.

It is another and/or alternative non-limiting object of the invention to provide a method for storing blood product and/or cellular culture in an easy and convenient way.

It is still another non-limiting object of the present invention to provide a method for storing blood product and/or cellular culture to deliver the exact amount of expensive gas as needed and to create the high pressure required for storage, and utilizing other inexpensive gas to obtain a designed pressure for preserving the blood product and/or cellular culture.

It is still another non-limiting object of the present invention to provide a method for storing blood product and/or cellular culture and to minimize the formation of aggregates of blood product and/or cellular culture during the storage of the blood product and/or cellular culture.

These and other objects and advantages will become apparent from the following description taken together with the accompanying drawings.

DETAILED DESCRIPTION OF NON-LIMITING EMBODIMENTS

Figure 1:
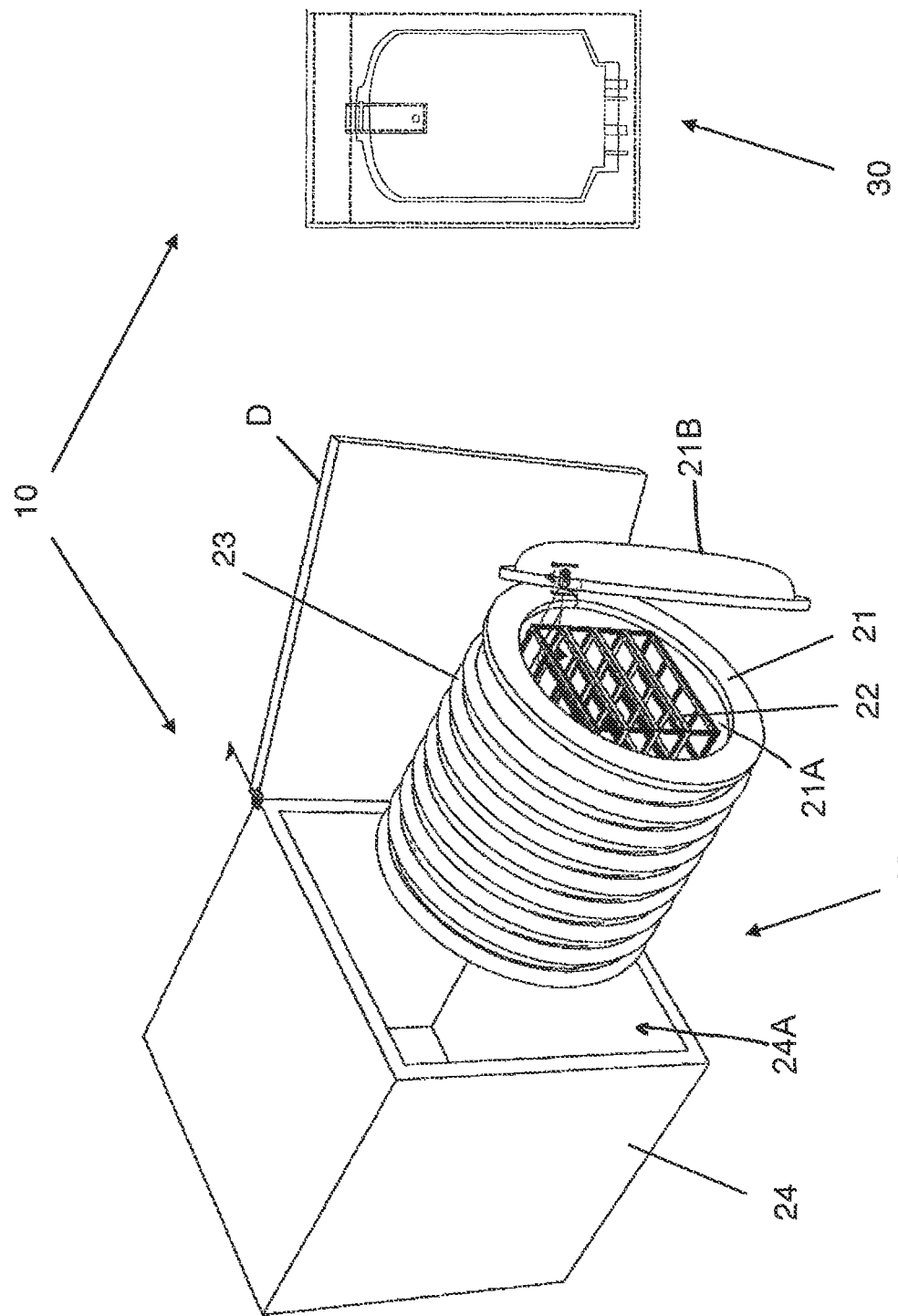
FIG. 1 illustrates an exploded view of one non-limiting blood product preservation device in accordance with the present invention.

Referring now to the drawings wherein the showings are for the purpose of illustrating non-limiting embodiments of the invention only and not for the purpose of limiting same, FIGS. 1-7 illustrate several non-limiting embodiments of the device for preserving blood product and/or cellular culture in accordance with the present invention.

Referring now to FIG. 1, the preservation device 10 includes a storage chamber 20 and a receptacle 30. The storage chamber can include housing 24 and a hermetically-sealable pressure chamber 21. The housing can optionally be thermo-insulated. The housing can optionally be hermetically sealable. The housing generally includes a door D that can be used to open and close the internal cavity 24A in the housing. The door can be lockable; however, this is not required. The housing can optionally include a refrigeration unit (not shown) to control the temperature of the internal cavity of the housing. The size and shape of the housing and the cavity of the housing is non-limiting. Generally, the size and shape of the cavity of the housing is selected so that the cavity can fully receive one or more hermetically-sealable pressure chambers 21, and that the door D (when used) can be fully closed while the hermetically-sealable pressure chamber is positioned in the cavity of the housing. The materials used to form the housing are non-limiting. Generally, one or more walls of the housing include or are formed of an insulation material so that the temperature of the cavity of the housing can be better maintained when the door on the housing is closed; however, this is not required.

Figure 5:
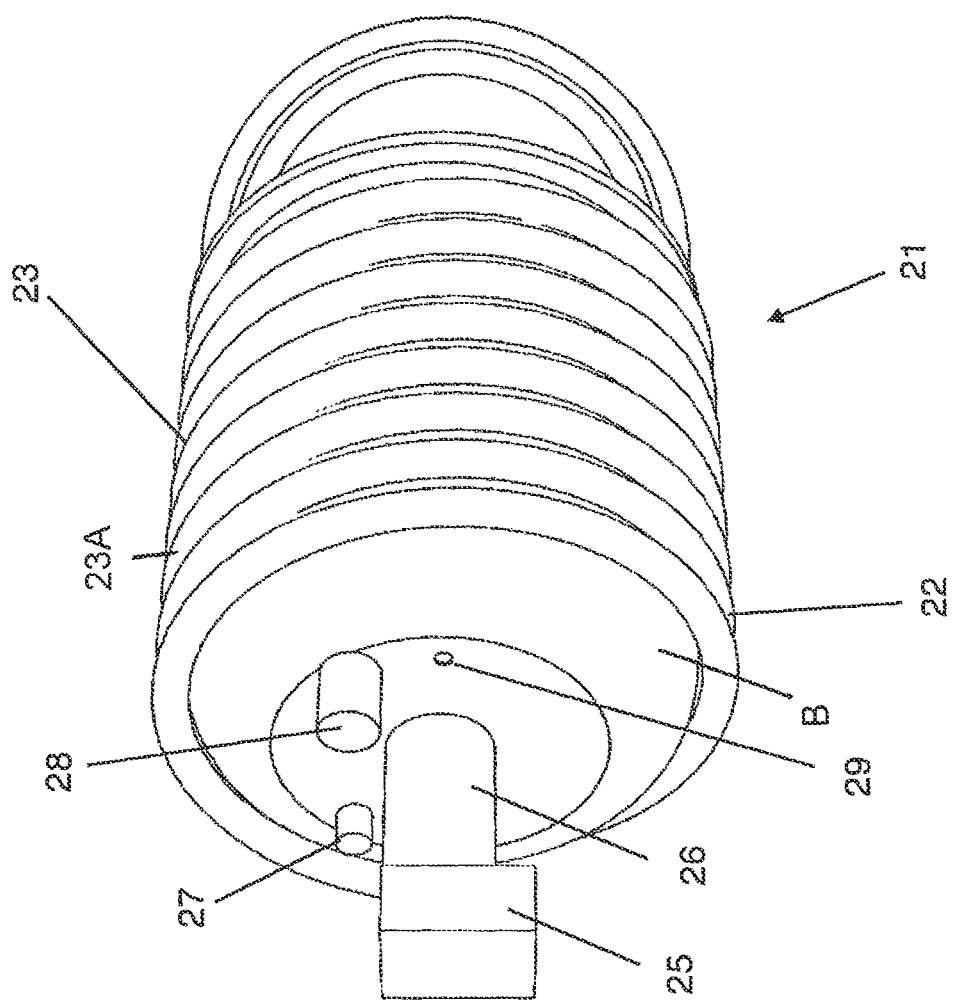
FIG. 5 is a back view of the chamber illustrated in FIG. 1 which illustrates an agitator arrangement, valves for a gas supply, and one or more sensors.

Referring now to FIGS. 1 and 5, the hermetically-sealable pressure chamber 21 is designed to withstand required high air pressure in the internal cavity of the hermetically-sealable pressure chamber so that when high pressures exist in the internal cavity of the hermetically-sealable pressure chamber, the hermetically-sealable pressure chamber does not leak gas, rupture or otherwise be caused to be damaged. High pressure is defined as at least 2 bars above ambient pressure (e.g., 1 atm.), typically at least 3 bars above ambient pressure, more typically at least 5 bars above ambient pressure.

The hermetically-sealable pressure chamber 21 can optionally include a cooling coil or cooling plate positioned on and/or wrapped around the hermetically-sealable pressure chamber to facilitate in the cooling of the hermetically-sealable pressure chamber. As illustrated in FIGS. 1 and 5, the outside surface 23 of the hermetically-sealable pressure chamber 21 can be formed of one or more cooling coils 23A. The cooling coils can be used to provide structural integrity to the hermetically-sealable pressure chamber, and/or be used to merely cool the internal cavity 21A of the hermetically-sealable pressure chamber. When the cooling coil and/or cooling plate is connected to the hermetically-sealable pressure chamber, the cooling coil and/or cooling plate is generally connected to refrigeration unit (e.g., refrigeration compressor, etc.). As can be appreciated, the housing 24 can also or alternatively include a refrigeration system used to maintain a desired temperature of the hermetically-sealable pressure chamber while positioned in the cavity of the housing. The hermetically-sealable pressure chamber can be formed of a heat conducting material (e.g., metal, etc.) to enable the internal cavity 21A of the hermetically-sealable pressure chamber to be rapidly cooled when the cavity is hermetically sealed; however, this is not required.

As illustrated in FIG. 1, the hermetically-sealable pressure chamber 21 includes a cylindrically shaped internal cavity 21A that is configured to receive a rack or shelve system 22; however, it can be appreciated that other shapes of the internal cavity can be used. A door 21B is used to hermetically seal the internal cavity. The door generally includes a sealing arrangement (e.g., seals, gaskets, etc.) and a lock or latch arrangement to secure the door in a closed position. As illustrated in FIG. 1, the door is connected to a hinge to enable the door to swing between an open and closed position; however, other arrangements can be used to enable the door to move between an open and closed position.

Referring now to FIG. 5, the back side B of one non-limiting hermetically-sealable pressure chamber 21 is illustrated. The hermetically-sealable pressure chamber can include one or more orifices (e.g., 1-5 orifices). For example, orifice 29 can optionally be used to suppling a gas (e.g., air)

into the internal cavity of the hermetically-sealable pressure chamber so as to enable the pressurization of the internal cavity when the hermetically-sealable pressure chamber is hermetically sealed. Orifice 29 can include be a one-way valve; however, this is not required. Orifice 29 can optionally be used to release gas from the internal cavity of the hermetically-sealable pressure chamber to thereby depressurize the internal cavity of the hermetically-sealable pressure chamber and/or to remove excessive pressure in the internal cavity of the hermetically-sealable pressure chamber. In one non-limiting arrangement, orifice 29 can be an electronic orifice than can be controlled to depressurize the internal cavity of the hermetically-sealable pressure chamber and/or automatically remove excess pressure from the internal cavity of the hermetically-sealable pressure chamber; however, this is not required. Orifice 29 can include be a one-way valve; however, this is not required. Orifice 27 can optionally be used to accommodate a temperature and/or a pressure sensor. As can be appreciated, if both a temperature and pressure sensor are used, each sensor can have its own orifice; however, this is not required. Optional orifice 26 is illustrated as being positioned along the central axis of the internal cavity of the hermetically-sealable pressure chamber; however, this is not required. Connected to the rear end of orifice 26 is an optional agitation unit 25. The agitation unit 25 generally includes a motor that is designed to rotate an axle. The body of the axle (not shown) generally passes through orifice 26 and into the internal cavity of the internal cavity of the hermetically-sealable pressure chamber; however, this is not required. The cavity of orifice 26 can optionally include a sealing arrangement and/or a support or bearing arrangement to support the axle and/or to facilitate in the rotation of the axle while preventing gas from passing through the orifice. As will be discussed below, a connection arrangement at the end of the axle is to be connected to rack or shelve system 22 to cause rack or shelve system 22 to be vibrated and/or rotated while positioned in the internal cavity of the hermetically-sealable pressure chamber; however, this is not required. As can be appreciated, additional orifices can optionally be used. For example, an orifice can optionally be used for a safety pressure check valve; however, this is not required. One or more orifices can be used to fluidly connect two of more hermetically-sealable pressure chambers that are positioned in the cavity 24A of housing 24; however, this is not required.

Figure 3:
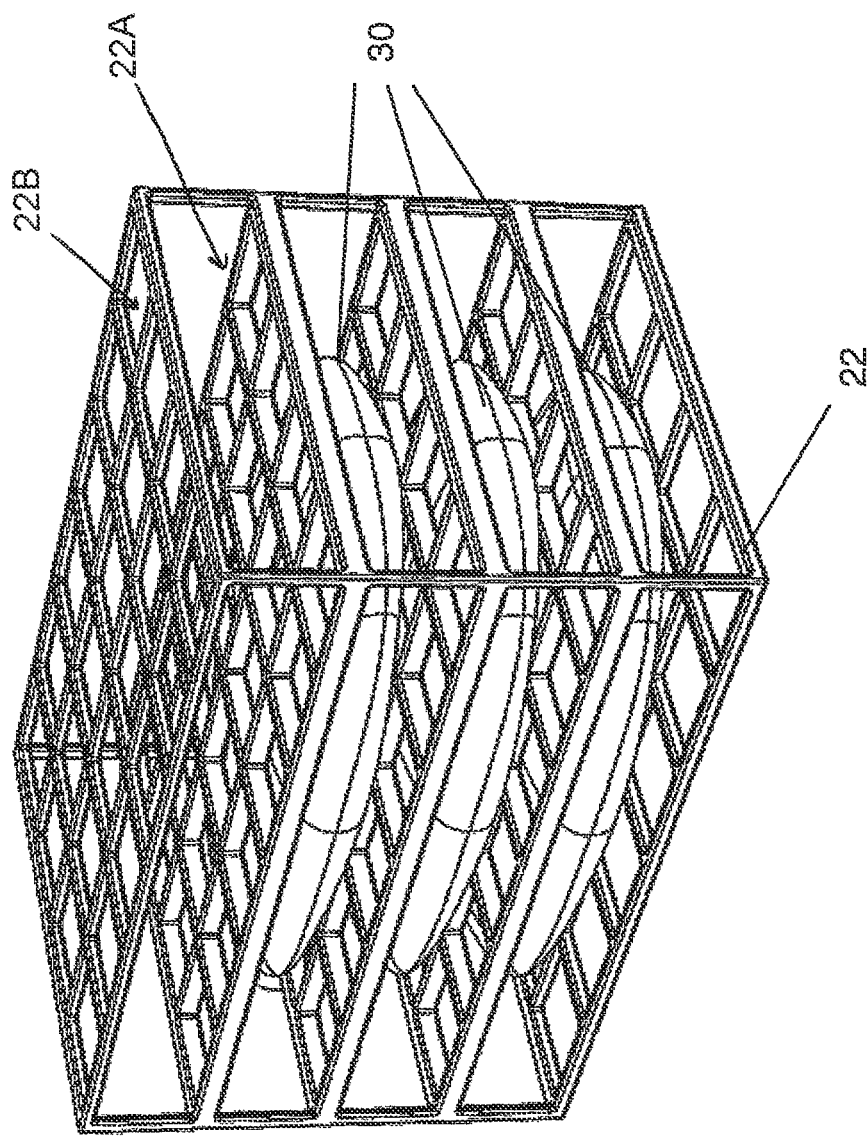
FIG. 3 illustrates a non-limiting design of the rack loaded with a plurality of receptacles.

As illustrated in FIGS. 1 and 3, a rack or shelve system 22 can optionally be used with the hermetically-sealable pressure chamber. The rack or shelve system can be used to support one or more receptacles in the hermetically-sealable pressure chamber 21. The rack or shelve system can be fixed in the hermetically-sealable pressure chamber or be movable with respect to the hermetically-sealable pressure chamber. In one non-limiting arrangement, the rack or shelve system can be connected to an agitation arrangement that causes the blood product and/or cellular culture in the receptacle to be agitated while being stored in the hermetically-sealable pressure chamber. In one non-limiting arrangement, the rack or shelve system can be releasably or non-releasably connected to an axle (not shown) that is located in the cavity of the hermetically-sealable pressure chamber. The axle can be caused to vibrate and/or rotate by an agitation unit 25 to thereby cause the rack or shelve system to vibrate and/or to rotate in the cavity of the hermetically-sealable pressure chamber, thereby providing agitation to the blood product and/or cellular culture in the receptacle. When the rack or shelve system is to be rotated in the cavity of the hermetically-sealable pressure chamber, the size and shape of the cavity of the hermetically-sealable pressure chamber and the size and shape of the rack or shelve system are selected to enable the rack or shelve system to rotated within the cavity of the hermetically-sealable pressure chamber without damaging the hermetically-sealable pressure chamber and the rack or shelve system. In such an arrangement, the rack or shelve system generally does not contact the side walls of the cavity of the hermetically-sealable pressure chamber, and can also optionally be spaced from the back wall and rear surface of the front wall or door of the hermetically-sealable pressure chamber. When the axle protrudes through the rear wall of the hermetically-sealable pressure chamber, an airtight bearing arrangement can be used to inhibit or prevent gas in the cavity of the hermetically-sealable pressure chamber from escaping the cavity when the hermetically-sealable pressure chamber is hermetically sealed. As can be appreciated, the chamber itself can be caused to vibrate and/or rotate by an agitation unit 25, thereby providing agitation to the blood product and/or cellular culture in the receptacle.

Referring now to FIG. 3, one non-limiting rack or shelve system 22 is illustrated. The rack or shelve system is illustrated as including four shelf cavities 22A that are each configured to hold one or more receptacles 30; however, it can be appreciated that the rack or shelve system can include any number of shelf cavities (e.g., 1, 2, 3, 4, 5, etc.). When the rack or shelve system is configured to be rotated in the cavity of the hermetically-sealable pressure chamber, the rack or shelve system can include a retention arrangement to maintain the one or more receptacles on the shelf cavity as the rack or shelve system so as to limit or prevent damage to the rack or shelve system and/or the one or more receptacles during the rotation of the rack or shelve system. Such retention arrangement can be in the form of the height and/or width of the shelf cavity, side walls on the shelf cavity, mechanical connectors, etc. The materials used to form the rack or shelve system are non-limiting. In one non-limiting embodiment, the rack or shelve system is formed of a plastic material or a lightweight metal (e.g., aluminum). As illustrated in FIG. 3, the top and base of each shelf cavity includes a plurality of openings 22B. These openings enable the temperature about each receptacle to be the same while the rack or shelve system and one or more receptacles are in the cavity of the hermetically-sealable pressure chamber. The number, size and shape of openings is non-limiting. The size of the openings should not be too large to allow the receptacle to pass thought the opening. As illustrated in FIG. 3, the size and shape of the openings is the same; however, this is not required. In one non-limiting configuration, the rack or shelve system is configured to provide compact accommodation of as many receptacles 30 as possible in the hermetically-sealable pressure chamber 21.

As can be appreciated, the storage chamber 20 can optionally include one or more other components such as a temperature control unit, a pressure control unit, a gas compressor, a refrigeration system, electronically-controlled valves, pressure and temperature sensors, power source, timer, electronic valves, electronic locks, automatic doors, etc.

Figure 2:
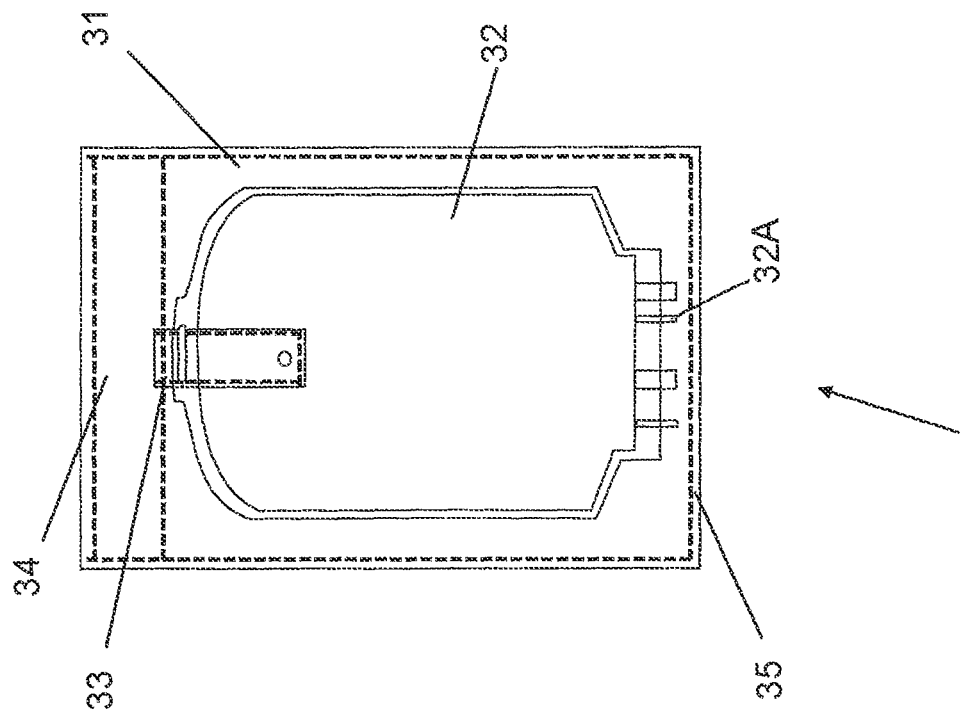
FIG. 2 illustrates a construction of a receptacle that includes a secondary bag with a conventional storage bag inside the secondary bag.

Referring now to FIGS. 1 and 2, there is illustrated a receptacle 30 that includes a secondary bag 31 and a conventional storage bag 32. The secondary bag is a flexible bag that includes a cavity that is configured to fully contain conventional storage bag 32 in the cavity of the secondary bag. The conventional storage bag can optionally be a conventional bag that is used to store blood (see for example http://www.jmsna.net/Catalogs/jms-bloodbag-en-r1.pdf).
The conventional storage bag is typically a flexible bag that includes a cavity for retaining blood product and/or cellular culture. The conventional storage bag includes one or more ports 32A at the bottom end of the bag that are used to allow flow into and/or out of the bag. Generally, the cavity of the conventional storage bag is filled with blood product and/or cellular culture prior to being sealed. After the blood product and/or cellular culture is sealed in the conventional storage bag, the conventional storage bag is inserted into the cavity of the secondary bag. After the conventional storage bag is inserted into the cavity of the secondary bag, the cavity of the secondary bag is hermetically sealed. The cavity of the secondary bag is configured such that the conventional storage bag does not need to be opened or otherwise have the integrity of the conventional storage bag compromised when the conventional storage bag is placed in the secondary bag.

The conventional storage bag and the secondary bag are formed of different materials. The conventional storage bag is formed of a flexible material that is permeable to at least xenon, or permeable to at least xenon and oxygen. The secondary bag is formed of a material and/or includes a film or coating that is not permeable to xenon and oxygen. Generally, the secondary bag is not permeable to xenon and any of the primary components of air (e.g., oxygen, nitrogen, carbon dioxide, water vapor, etc.).

The secondary bag can be formed by use of an adhesive or heat seal 35 about the perimeter of the secondary bag; however, this is not required. Generally, the secondary bag is open at the top end so that the conventional storage bag can be inserted into the cavity of the secondary bag. Thereafter, the top of the secondary bag can be sealed by forming a seal 34 (e.g., seal formed by adhesive, heat formed seal, etc.). After the conventional storage bag is inserted into the cavity of the secondary bag and prior to, during, or after the hermetic sealing of the cavity of the secondary bag while the cavity fully contains the conventional storage bag, a gas system is added to the cavity of the secondary bag. The gas system can be added via gas inlet 33 that is formed on secondary bag 31. The gas inlet can be connected to a gas filling tube which is in turn connected to a source of the gas system. The gas inlet can be in the form of a nipple that is made as a soft sleeve; however, this is not required. The gas inlet can be sealable and/or includes a valve so as to prevent gas from passing through the gas inlet after the cavity of the secondary bag has been filled with the gas system. The gas inlet can be designed to allow the gas system to freely flow into the cavity of the secondary bag when a gas supply tube is inserted in the sleeve of the gas inlet due to the gas pressure opening the sleeve. When the gas tube is removed from the sleeve of the gas inlet, the gas backpressure inside the cavity of the secondary bag can be designed to seal the sleeve and thereby prevent the gas from escaping the cavity of the secondary bag. The top portion of the secondary bag is generally sealed prior to the complete filling of the cavity of the secondary bag with the gas system. Generally, the gas pressure in the cavity of the secondary bag is about 0.5-5 bars above atmospheric pressure (e.g., 1 atm.). The gas system generally includes xenon. The gas system can include one or more additional gasses such as oxygen and/or carbon dioxide.

Figure 4:
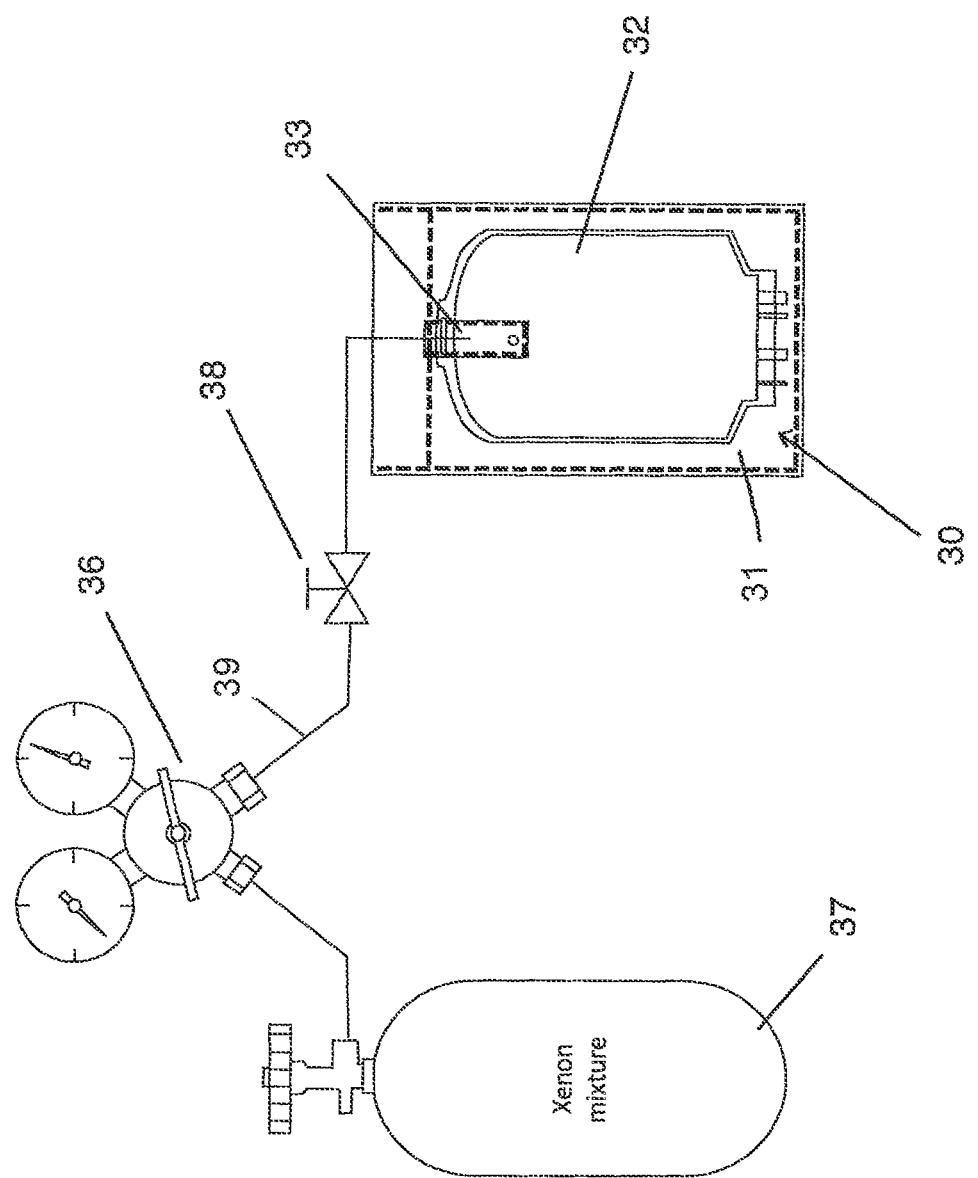
FIG. 4 illustrates one non-limiting setup for filling the secondary bag of the receptacle with a gas system.

Referring now to FIG. 4, there is illustrated a non-limiting arrangement for inserting a gas system into the cavity of the secondary bag. The receptacle 30 is in the form of a secondary bag 31 that includes a conventional storage bag 32 that is designed to include a blood product and/or cellular culture. A gas canister 37 that includes pressurized gas system provides the source of gas system to be inserted into the receptacle. A gas regulator 36 (e.g., pressure reducer) can be optionally used. The gas regulator is connected between the gas canister and valve 38 by a gas supply tube 39. The insertion of the gas system into receptacle 30 can be by manual operation or the preselected volume gas can be automatically inserted into the receptacle and/or the cavity of the secondary bag can be automatically pressurized to a preselected pressure by the insertion of the gas system into the cavity of the secondary bag. The end of the gas supply tube can be inserted to the gas inlet 33 of the secondary bag 31 so that the gas system can be inserted into the cavity of the secondary bag. As can be appreciated, other or additional arrangements of the gas feeding system can be used.

Figure 6:
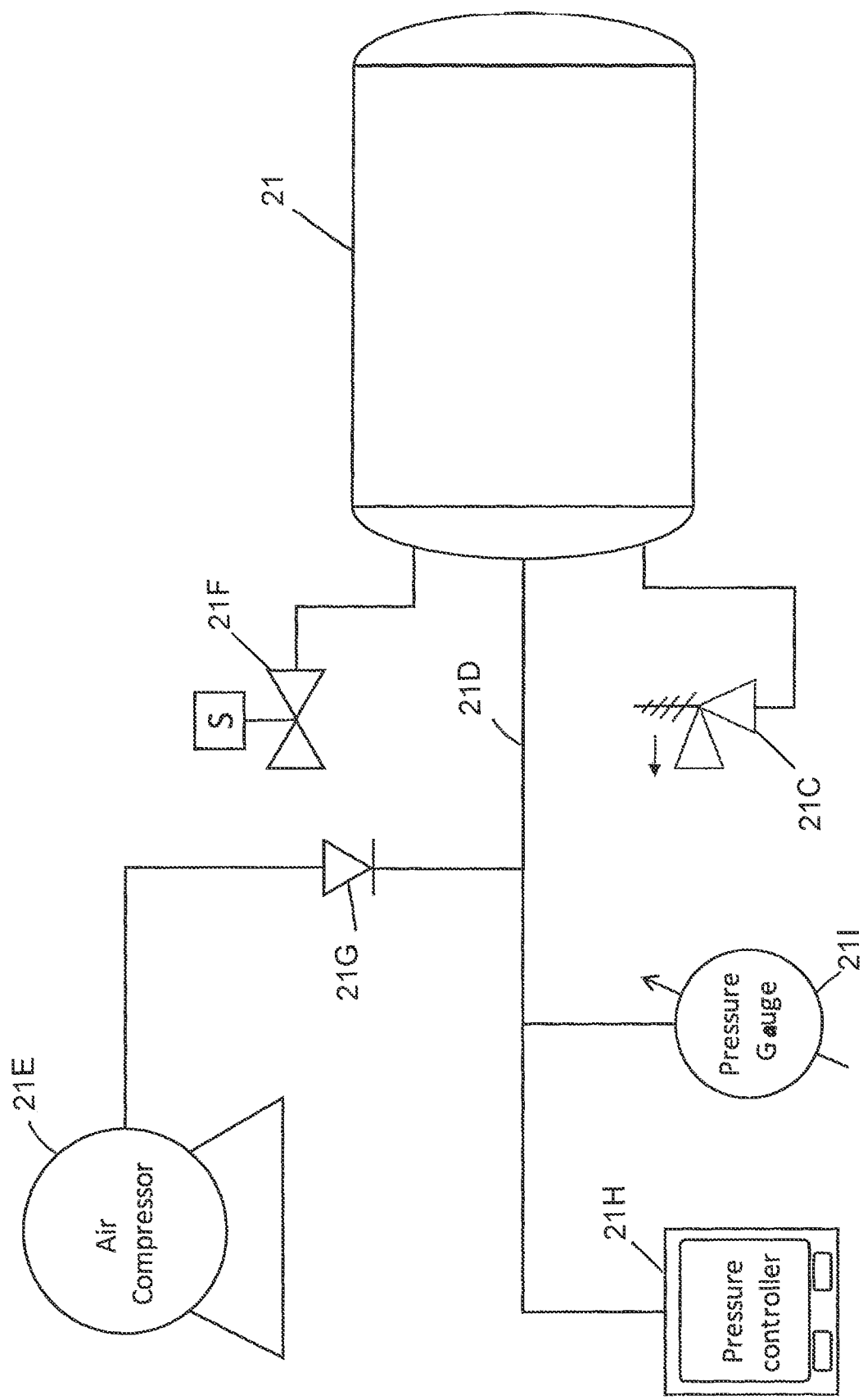
FIG. 6 illustrates a non-limiting compressed air diagram for connecting a gas compressor to pressurize the chamber of FIG. 5; and, FIG. 7 illustrates a non-limiting diagram for a control and operation arrangement for the storage chamber illustrated in FIG. 1.

Referring now to FIG. 6, there is illustrated a non-limiting example of a system for pressurizing the internal cavity 21A of the hermetically-sealable pressure chamber 21. Once the receptacle 30 or the rack or shelve system that includes one or more receptacles is hermetically sealed in the internal cavity 21A of the hermetically-sealable pressure chamber, the pressure in the internal cavity of the hermetically-sealable pressure chamber is increased. Generally, the pressure is increased to 1-10 bars above ambient pressure (e.g., 1 atm.). As illustrated in FIG. 6, the hermetically-sealable pressure chamber is connected to a drain or pressure relief valve 21C, a high-pressure air line 21D from an air compressor 21E, and a safety check valve 21F. The safety check valve can be used to prevent over pressurization of the internal cavity of the hermetically-sealable pressure chamber. The pressure relief valve can be used to reduce pressure or fully depressurize the pressure in the internal cavity of the hermetically-sealable pressure chamber. The air compressor is designed to pressure a gas such as air or another type of gas and pressure air line 21D and through a one way valve 21G and then into the internal cavity of the hermetically-sealable pressure chamber. A pressure controller 21H can be configured to monitor the pressure value generated by the pressure gauge 21I which represents the pressure in the internal cavity of the hermetically-sealable pressure chamber. The pressure controller can be used to control the operation of the air compressor 21E and/or pressure relief valve 21C and/or safety valve 21F to control and/or maintain a desired pressure (e.g., preset pressure, etc.) in the internal cavity of the hermetically-sealable pressure chamber. For example, if the pressure in the internal cavity of the hermetically-sealable pressure chamber drops lower than preset level due to potential leaks in the chamber and/or lines, the pressure controller can be designed to cause the activation of the air compressor to restore the desired pressure inside the internal cavity of the hermetically-sealable pressure chamber to the preset pressure level. Also, the pressure controller can cause the pressure relief valve to open when the pressure controller determines that the pressure in the internal cavity of the hermetically-sealable pressure chamber is higher than the preset pressure value.

Figure 7:
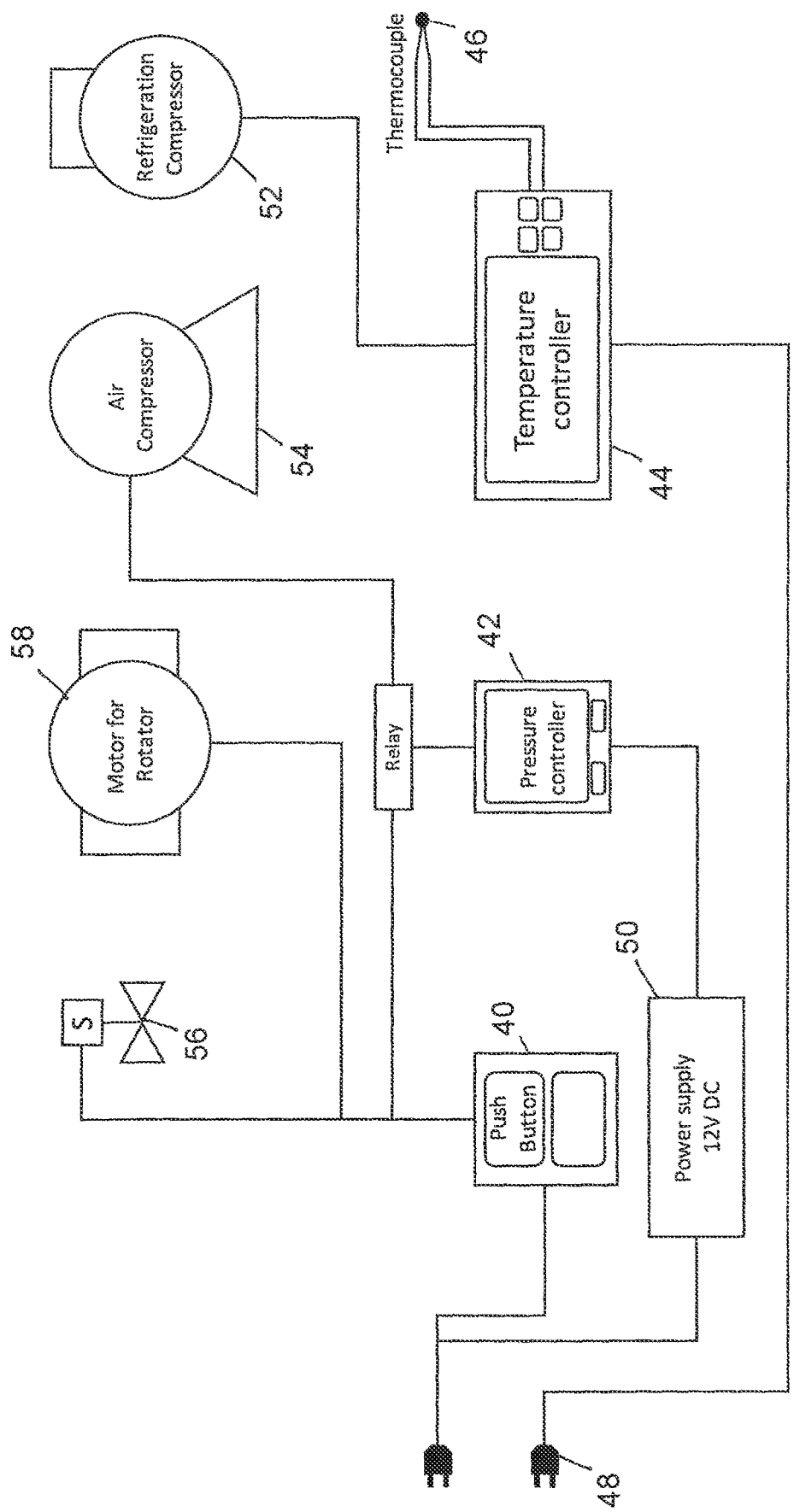

Referring now to FIG. 7, there is illustrated a non-limiting electrical diagram of the internal cavity of the hermetically-sealable pressure chamber for controlling the preservation of the blood products and/or cellular culture in the hermetically-sealable pressure chamber. After the receptacle 30 or the rack or shelve system that includes one or more receptacles is hermetically sealed in the internal cavity 21A of the hermetically-sealable pressure chamber, an operator can then press the start or push button 40 that causes the pressure controller 42 and temperature controller 44 to cause the pressure in the internal cavity 21A of the hermetically-sealable pressure chamber to increase to a preset level and to cause the temperature in the internal cavity 21A to decrease to a preset level. A thermocouple 46 is used to measure the temperature in the internal cavity 21A and to provide such information to the temperature controller. When the temperature controller determines that the temperature in the internal cavity is less than the preset temperature, the temperature controller causes the refrigeration compressor 52 to activate and to cause cooling the internal cavity of the housing that includes the hermetically-sealable pressure chamber. Once the temperature in the cavity of the housing and/or in internal cavity 21A of the hermetically-sealable pressure chamber reaches the desired preset temperature, the temperature controller causes the refrigeration compressor to stop. Likewise, a pressure sensor is used to measure the pressure in the internal cavity 21A and to provide such information to the pressure controller. When the pressure in the internal cavity 21A of the hermetically-sealable pressure chamber falls below a preset pressure, the pressure controller causes the air compressor 54 to activate to increase the pressure in the internal cavity 21A of the hermetically-sealable pressure chamber. Once the pressure in the internal cavity 21A reaches the preset pressure, the pressure controller causes the air compressor to stop. If the pressure in the internal cavity 21A exceeds the preset pressure, the pressure controller can cause the pressure relief valve 21C to release pressure from the internal cavity 21A. During the storage of the one or more receptacles in the internal cavity 21A, a motor 58 of the agitation device is activated to cause agitation of the blood product and/or cellular culture in the receptacle during the preservation of the blood product and/or cellular culture in the receptacle. A power source 48 and/or power supply 50 is used to supply power to the components of the control system.

The above-described device can be used to preserve and store blood products and/or cellular culture. The device of the present invention can be used when implementing blood product preservation methods described in U.S. Pat. No. 8,158,339, which is incorporated herein by reference.

In accordance with the present invention, the preservation device can function as follows:

A blood product (e.g., platelet concentrate, whole blood, packed red blood cells) and/or cellular culture is placed in a conventional storage bag made of gas-permeable material. Depending on the gas system (a pure gas, a gas system composition) used to preserve the blood product and/or cellular culture, a material used for conventional storage bag should have the desired gas permeability to the gas system. Specifically, when implementing the preservation method of the present invention which involves the use of xenon or a xenon mixture, a bag material for the conventional storage bag should be permeable to xenon. For example, conventional storage bags for platelet concentrate produced by TerumoBCT (Lakewood, Colo.) or Haemonetics (Braintree, Mass.) have the desired xenon permeability features that are required of the conventional storage bag for use in the present invention. Blood products and/or cellular cultures that are to be preserved in accordance with the present invention can be obtained through the use of well-known methods and appropriate available equipment.

The hermetically-sealed conventional storage bag 32 that contains the blood product and/or cellular culture is placed into the cavity of the secondary bag 31. Thereafter, the secondary bag is sealed to hermetically seal the conventional storage bag in the cavity of the secondary bag. By utilizing the set up illustrated in FIG. 4, the secondary bag is filled with the gas system that is required in compliance with the used preservation method. The gas system (e.g., pure xenon or a mixture that contains xenon) is inserted into the cavity of the secondary bag through the gas inlet 33. The gas pressure inserted into the cavity of the secondary bag is at a pressure which is to equal or a higher than atmospheric pressure. For example, the secondary bag is generally filled with the gas system such that the pressure in the cavity of the secondary bag is at a pressure of 0.0001-10 bars (and all values and ranges therebetween) above ambient pressure (e.g., 1 atm. at sea level). In one specific embodiment, the secondary bag is filled with the gas system such that the pressure in the cavity of the secondary bag is at a pressure of 0.1-5 bars above ambient pressure, typically 0.1-4 bars above ambient pressure, more typically 0.1-3 bars above ambient pressure, still more typically 0.1-2 bars above ambient pressure, and yet still more typically 0.1-1 bar above ambient pressure. The secondary bag is inflated by the gas system until the gas feeding is terminated automatically by the filling system or manually when the secondary bag visually appears fully inflated. To ensure the hermetic seal of the secondary bag during prolonged storage after filling, the secondary bag can be sealed along the opposite edge 34.

After filling the cavity of the secondary bag with the required amount of gas system, the secondary bag containing conventional storage bag with the blood product and/or cellular culture is placed in the internal cavity 21A of the hermetically-sealable pressure chamber. In one non-limiting embodiment of this invention, the receptacle can be placed on the shelf of the rack 22. The pressure chamber 21 is then hermetically closed and the storage cycle is engaged. The gas release valve 21C closes and the air compressor 21E starts building pressure in the pressure chamber by feeding air or some other gas into the internal cavity 21A of the hermetically-sealable pressure chamber. When air pressure inside internal cavity 21A reaches a preset pressure level, the air compressor stops. In one non-limiting embodiment, the pressure in the sealed cavity of the hermetically-sealable pressure chamber generally reaches a pressure of 0.0001-20 bars (and all values and ranges therebetween) above ambient pressure (e.g., 1 atm. at sea level). In one specific embodiment, the sealed cavity of the hermetically-sealable pressure chamber is pressurized to a pressure of 0.5-10 bars above ambient pressure, typically 1-6 bars above ambient pressure, more typically 1-5 bars above ambient pressure, still more typically 2-5 bars above ambient pressure, and yet still more typically 3.5-5 bars above ambient pressure. In one non-limiting arrangement, the pressure to which the cavity of the secondary bag is filled with the gas system prior to the secondary bag being inserted into the cavity of the hermetically-sealable pressure chamber is equal to or less than the pressure in the sealed cavity of the hermetically-sealable pressure chamber after the sealed cavity of the hermetically-sealable pressure chamber has been fully pressurized. In another non-limiting arrangement, the pressure to which the cavity of the secondary bag is filled with the gas system prior to the secondary bag being inserted into the cavity of the hermetically-sealable pressure chamber is less than the pressure in the sealed cavity of the hermetically-sealable pressure chamber after the sealed cavity of the hermetically-sealable pressure chamber has been fully pressurized.

The pressure chamber 21 also may be cooled with the refrigeration compressor 52 until the preset temperature is obtained in the internal cavity. Alternatively, the pressure chamber can be placed in the refrigerator or cold room. During the storage of the one or more receptacles in the cavity of the hermetically-sealable pressure chamber, the temperature in the cavity of the hermetically-sealable pressure chamber is generally less than about 15° C. and above the freezing point of the blood product and/or cellular culture in the receptacle. In one non-limiting arrangement, the cavity of the hermetically-sealable pressure chamber is cooled to a temperature of 0.01-15° C., typically 1-10° C., and more typically 3-6° C.

When the air pressure outside the secondary bag increases due to the pressure in the internal cavity 21A increasing, the gas system in the cavity of the secondary base is caused to equilibrate, thereby causing additional gas system to penetrate into the conventional storage bag to increase the amount of gas system in the blood product and/or cellular culture. Therefore, the conditions are created for higher solubility of the gas system in the blood product and/or cellular culture. Also, when the pressure chamber is hermetically closed, the agitation arrangement can be activated to cause the rack to vibrate or rotate inside the internal cavity 21A to achieve the desired agitation of a blood product and/or cellular culture during storage.

When one or more receptacles are to be removed from storage from the cavity of the hermetically-sealable pressure chamber, the elevated pressure in the hermetically-sealable pressure chamber can be optionally partially or fully released prior to the door 21B to the chamber 21. The drain or pressure relief valve 21C can be used to reduce the pressure in the internal cavity 21A of chamber 21. Once the elevated pressure in the internal cavity 21A of chamber 21 is reduced, door 21B is opened and one or more receptacles are removed from the internal cavity 21A of chamber 21. Thereafter, the receptacle is generally allowed to partially or fully warm up to room temperature prior to the use of the blood product and/or cellular culture in the conventional storage bag 32. During the warming of the blood product and/or cellular culture in the conventional storage bag 32, the gas system concentration inside the conventional storage bag equalizes with concentration of gasses in the ambient atmosphere (e.g., air). In one non-limiting arrangement, the conventional storage bag 32 is left in the secondary bag 31 during the time period that the blood product and/or cellular culture in the conventional storage bag 32 partially or fully warms to room temperature. In another non-limiting arrangement, the conventional storage bag 32 is removed from the secondary bag 31 during the time period that the blood product and/or cellular culture in the conventional storage bag 32 partially or fully warms to room temperature. The secondary bag is opened (e.g., cutting open, etc.) without damaging the conventional storage bag 32 to enable the conventional storage bag 32 to be removed from the cavity of the secondary bag. Thereafter, the secondary bag can be deposed of since it is not designed to be reused. Generally, the warming of the blood product and/or cellular culture in the conventional storage bag 32 is by natural warming. Heating of the blood product and/or cellular culture in the conventional storage bag 32 by a heater, oven or other type of heating devices is generally not used. After the blood product and/or cellular culture in the conventional storage bag 32 has warmed to a desired temperature and the gas system concentration inside the bag conventional storage bag has partially or fully equalized with concentration of gasses in the ambient atmosphere, the blood product and/or cellular culture can be used in a transfusion or other type of procedure.

Example 1

A conventional storage bag containing platelet concentrate is first placed into the cavity of secondary bag 31. Thereafter, a gas feeding system is connected to gas inlet 33 of the secondary bag. A gas system containing xenon (e.g., at least 50-65% xenon) is inserted into the cavity of the secondary bag. Due to the fact that conventional platelet storage bags are made of gas-permeable material for xenon, the platelet concentrate contained in the conventional storage bag 32 is saturated with the gas system, and thereby creates conditions (namely, composition, pressure exerted by gas system, and temperature) to provide preservation of the platelet concentrate in the conventional storage bag. Subsequently, the sealed secondary bag is placed in the internal cavity 21A of chamber 20. The door 21B is then closed to seal the chamber. Thereafter, the internal cavity 21A is subjected to the elevated air pressure (e.g., 3.5-5 bars above ambient pressure) and to refrigeration temperature (e.g., 3-6° C.). The secondary bag is positioned in the internal cavity 21A such that the conventional storage bag lies in a horizontal position. The secondary bag can also be rotated such that the conventional storage bag located in the cavity of the secondary bag rotates about its longitudinal axis. Such rotation is designed to keep the platelets suspended during storage without imposing significant stress to the cells. Such rotation also eliminates sedimentation of the cells during prolonged storage and, as a consequence, reduces or eliminates aggregate formation. However, if necessary, the secondary bag can be stored at a different orientation in the internal cavity of the chamber.

When the secondary bag is to be removed from the internal cavity of the chamber, the air pressure in the chamber is released, the door 21B is opened and the secondary bag is removed from the internal cavity of the chamber. Thereafter, the conventional storage bag is removed from the cavity of the secondary bag. Prior to using the platelet concentrate in the conventional storage bag, the conventional storage bag can be kept at ambient temperature and pressure for a certain time period until the platelets warm up naturally (e.g., to room temperature) and the gas concentration of the gas system inside the conventional storage bag partially of fully equalizes with the ambient atmospheric concentration (e.g., air at sea level, etc.). Thereafter, the conventional storage bag containing the platelets can be used in a transfusion or other type of medical procedure.

Example 2

A platelet concentrate (not shown) is placed in a conventional storage bag made of material that is at least permeable to xenon and oxygen. For example, conventional storage bags for platelet concentrate storage produced by TerumoBCT (Lakewood, Colo.) could be used for this purpose. The conventional storage bag containing the platelet concentrate is hermetically sealed.

The hermetically-sealed conventional storage bag with platelet concentrate is placed in the cavity of the secondary bag 31, which is thereafter hermetically-sealed. After the secondary bag is sealed, a gas filling system is connected to gas inlet 33 so that a gas system can be inserted into the cavity of the secondary bag. A gas system is a xenon system, xenon and oxygen system (e.g., 79-95 vol. % xenon and 5-21 vol. % oxygen), xenon and one or more other gas system (e.g., air, oxygen, nitrogen, etc.), etc. can be used. During the insertion of the gas system into the cavity of the secondary bag, the secondary bag is caused to inflate. The introduction of the gas system into the cavity of the secondary bag is terminated manually or automatically by the filling system when the secondary bag visually appears fully inflated. Generally, the pressure in the cavity of the secondary bag is less than 1 bar above ambient pressure when the filling of the secondary bag with the gas system is terminated. Thereafter, the secondary bag is disconnected from the gas source, and the secondary bag is hermetically sealed. The system for feeding the gas system illustrated in FIG. 4 can be used to fill the cavity of the secondary bad with the gas system. The gas canister 37 in FIG. 4 can be a high-pressure bottle containing the gas system. As can be appreciated, other or additional arrangements for feeding the gas system into the cavity of the secondary bag can be used. The step of feeding the gas system into the cavity of the secondary bag 31 can be at a temperature of the ambient environment (e.g., 20-24° C.); however, other temperatures can be used.

Due to the fact that the conventional platelet storage bags are made of gas-permeable material for xenon, the platelet concentrate contained in the conventional storage bag 32 is saturated with the gas system, and creates conditions (namely, composition, pressure exerted by gas system and temperature) to provide preservation of the platelet concentrate in the conventional storage bag.

Subsequently, the sealed secondary bag is placed in the internal cavity 21A of chamber 20. The door 21B is then closed to seal the chamber. Thereafter, the internal cavity 21A is subjected to the elevated air pressure (e.g., 3.5-5 bars above ambient pressure) and to refrigeration temperature (e.g., 3-6° C.). The secondary bag is positioned in the internal cavity 21A such that the conventional storage bag lies in a horizontal position. The secondary bag can also be rotated such that the conventional storage bag located in the cavity of the secondary bag rotates about its longitudinal axis. Such rotation is designed to keep the platelets suspended during storage without imposing significant stress to the cells. Such rotation also eliminates sedimentation of the cells during prolonged storage and, as a consequence, reduces or eliminates aggregate formation. However, if necessary, the secondary bag can be stored at a different orientation in the internal cavity of the chamber.

When the secondary bag is to be removed from the internal cavity of the chamber, the air pressure in the chamber is released, the door 21B is opened and the secondary bag is removed from the internal cavity of the chamber. Thereafter, the conventional storage bag is removed from the cavity of the secondary bag. Prior to using the platelet concentrate in the conventional storage bag, the conventional storage bag can be kept at ambient temperature and pressure for a certain time period until the platelets warm up naturally (e.g., to room temperature) and the gas concentration of the gas system inside the conventional storage bag partially of fully equalizes with the ambient atmospheric concentration (e.g., air at sea level, etc.). Thereafter, the conventional storage bag containing the platelets can be used in a transfusion or other type of medical procedure.

The method in accordance with the present invention enables one to store a platelet concentrate more efficiently, prevent the platelets from sticking together, and not impair the functional properties of the platelets. The aphaeresis platelet concentrate (obtained through the use of standard methods) and standard plastic bags intended for platelet concentrate storage could be used with the method in accordance with the present invention. The absence of a dense deposit at the end of storage period allows for improved quality and safety of platelet concentrate that is transfused to patients.

The use of the device and method in accordance with the present invention is characterized by certain conveniences and can be used to accelerate the process of blood product preservation. With the proposed approach in accordance with the present invention, any receptacle 30 in the storage chamber 21 can be taken out, while other receptacles 30 remain in storage in the chamber 21. After removal of a receptacle from the chamber, the pressure and temperature conditions in chamber 21 can be restored for the continued storage of remaining receptacles in the chamber.

Thus, the present invention represents a device and method for preserving blood products and/or cellular cultures in a gas medium under pressure, which offers a number of advantages as compared to known prior art devices. The device in accordance with the present invention has been developed that functions as an all-purpose, reliable, easy-to-manufacture, easy-to-use, and inexpensive-to-use device. Since the hermetically-sealed secondary bag comes in contact with a conventional storage bag that contains blood product and/or cellular culture, the secondary bag is generally made as a single-use unit. As such, the secondary bag can be formed of low-cost materials and have a simple design that uses a small amount of material for manufacturing. The arrangement used in the present invention does not require the secondary bag or the convention storage bag to be designed to withstand high internal pressures. The elevated pressure in the internal cavity of the chamber during storage creates an outside or external pressure on the secondary bag which in turn causes the gas system in the cavity of the secondary bag to equilibrate with the gas pressure inside the conventional storage bag. Due to the fact that the secondary bag is flexible and can be opened along the entire edge of the bag, it is possible to easily place a conventional storage bag into the cavity of the secondary bag and then hermetically seal the secondary bag. At the same time, the shape and size of the secondary bag can be optionally configured to closely match the shape and size of the conventional storage bag. Generally the cavity of the secondary bag is larger than the conventional storage bag so that a space is left inside the secondary bag after the conventional storage bag is inserted into the cavity of the secondary bag to enable the gas system to be thereafter inserted into the cavity of the secondary bag. This space, when small, results in considerable saving of gas system used for the preserving of blood product and/or cellular culture. Generally, the volume of the cavity of the secondary bag is about 2-50% greater (and all values and ranges therebetween) than the volume of the conventional storage bag. In one non-limiting configuration, the volume of the cavity of the secondary bag is about 2-30% greater than the volume of the conventional storage bag, typically the volume of the cavity of the secondary bag is about 2-20% greater than the volume of the conventional storage bag, and more typically the volume of the cavity of the secondary bag is about 5-15% greater than the volume of the conventional storage bag.

Another advantage of the device and method in accordance with the present invention is that the pressure in the internal cavity of the chamber can be a different and less expensive gas than the gas system contained in the cavity of the secondary bag. As such, the opening and closing of the chamber, and/or repressurizing of the chamber due to leaks in the chamber can be simply and cheaply accomplished by merely adding pressurized air or some other inexpensive gas to the internal cavity of the chamber. Such a device has a significant advantage in comparison with other prior art the storage systems wherein high pressure of the gas system is used to create the desired gas pressure in the storage system.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

What is claimed:

1. A method for preserving platelets in a platelet concentrate for later use in an organism, said method comprising:
    providing a receptacle that includes a secondary bag and a storage bag, said secondary bag including a sealable secondary bag cavity, said storage bag including a sealable storage cavity containing the platelet concentrate, said storage bag being permeable to a gas system, said secondary bag being impermeable to said gas system when said storage bag is sealed in said secondary bag cavity of said secondary bag;
    inserting said storage bag into said secondary bag cavity;
    sealing said secondary bag cavity;
    inserting said receptacle into a chamber cavity;
    operating a refrigeration arrangement to reduce a temperature of the chamber cavity to a refrigerated temperature range between about 15 degrees Celsius and a freezing temperature of the platelet concentrate; and
    operating an agitation arrangement to rotate said receptacle
    while said receptacle is contained within the chamber cavity and the temperature of the chamber cavity is within the refrigerated temperature range.

2. The method as defined in claim 1, wherein said chamber cavity includes a cavity opening configured to enable said receptacle to be inserted and removed from said chamber cavity, said chamber cavity including an opening closure configured to move between and an open and closed position, said opening closure in said closed position configured to close said cavity opening and to inhibit or prevent gas from exiting said cavity opening.

3. The method as defined in claim 2, wherein said chamber cavity is configured to maintain a pressure above ambient pressure when said opening closure is in said closed position.

4. The method as defined in claim 2, wherein said chamber includes one or more orifices to enable a gas to be inserted into the chamber cavity, removed from the chamber cavity, or a combination thereof when said opening closure is in said closed position.

5. The method as defined in claim 1, wherein said refrigeration arrangement includes one or more refrigeration coils, one or more refrigeration plates, Peltier cooler, or combinations thereof located on an outer surface of said chamber, on an inner surface of said chamber cavity, or combinations thereof.

6. The method as defined in claim 1, wherein the refrigeration arrangement includes a refrigeration housing that includes a housing cavity, said housing cavity configured to at least partially contain said chamber.

7. The method as defined in claim 1, further comprising a rack system, said rack system configured to be at least partially inserted into said chamber cavity, said rack system including one or more shelfs, each of said shelfs configured to support one or more of said receptacles in said rack system.

8. The method as defined in claim 7, wherein said agitation arrangement is configured to rotate said rack system while said rack system is at least partially contained in said chamber cavity.

9. The method as defined in claim 1, wherein said secondary bag is at least partially formed of a flexible material.

10. The method as defined in claim 1, wherein said secondary bag is impermeable to xenon and air when said storage bag is sealed in said secondary bag cavity, and said storage bag is permeable to xenon.

11. The method as defined in claim 1, wherein said secondary bag is a disposable plastic bag that is configured to be disposed of after said storage bag is removed from said secondary bag cavity.

12. The method as defined in claim 1, wherein said secondary bag cavity includes said gas system.

13. The method as defined in claim 12, wherein a pressure of said gas system in said secondary bag cavity is less than 4 bar when said receptacle is outside said chamber cavity.

14. The method as defined in claim 1, wherein said secondary bag includes a gas inlet configured to enable said gas system to be inserted into said secondary bag cavity while said storage bag is at least partially inserted in said secondary bag cavity, said gas inlet configured to be sealable to prevent said gas system in said secondary bag cavity from exiting said secondary bag cavity via said gas inlet.

15. A method for storing biological material comprising:
    providing a receptacle that includes a secondary bag and a storage bag, said storage bag including a sealable storage cavity containing the biological material to be preserved;
    inserting said storage bag into a secondary bag cavity of said secondary bag;
    sealing said secondary bag cavity;
    introducing a gas system including at least 5 vol. % xenon into said secondary bag cavity to a first pressure, said storage bag being permeable to said gas system, said secondary bag being impermeable to said gas system while said storage bag is sealed in said secondary bag cavity of said secondary bag;
    providing a chamber that includes a chamber cavity, said chamber cavity configured to at least partially contain one or more of said receptacles;
    inserting said receptacle into said chamber cavity;
    sealing said receptacle in said chamber cavity; and
    increasing a pressure in said chamber cavity to a second pressure greater than the first pressure by inserting a chamber gas into said chamber cavity, said secondary bag impermeable to said chamber gas, wherein chamber gas acts on the secondary bag to cause the gas system to penetrate into the storage bag to at least partially saturate the biological material with xenon,
    wherein said chamber gas has a different composition than said gas system.

16. The method as defined in claim 15, further comprising the steps of:

cooling said chamber cavity to a refrigerated temperature range between about 15 degrees Celsius and a freezing temperature of the biological material to be preserved; and rotating said receptacle within the chamber cavity while a temperature of the chamber cavity is in the refrigerated temperature range.

17. The method as defined in claim 15, wherein said chamber gas is compressed air.

18. The method as defined in claim 15, wherein said first pressure is no more than 4 bars above ambient pressure, and wherein said second pressure is no more than 20 bars above ambient pressure.

19. The method as defined in claim 15, wherein said secondary bag includes a gas inlet configured to enable said gas system to be inserted into said bag cavity while said storage bag is at least partially inserted in said bag cavity, said gas inlet configured to be sealable to prevent said gas system in said bag cavity from exiting said bag cavity via said gas inlet.

20. The method as defined in claim 15, including the step of inserting said chamber in a housing cavity of a thermally insulated housing during storage of said receptacle in said chamber.

21. The method as defined in claim 15, including the step of providing a rack system that includes at least one shelf, said rack system configured to be inserted in said cavity chamber, said shelf configured to support at least one said receptacle.

22. The method as defined in claim 21, wherein said rack system is connected to an agitation arrangement, said agitation arrangement configured to rotate said rack system while said rack system is contained in said chamber cavity.

23. The method as defined in claim 15, wherein said chamber is connected to an agitation arrangement, said agitation arrangement configured to rotate said chamber while said receptacle is inserted in said chamber cavity.

24. A method for preserving platelets in a platelet concentrate for later use in an organism, the method comprising:
providing a receptacle including a storage bag, the storage bag including a sealable storage cavity containing the platelet concentrate;
operating a refrigeration unit configured to reduce a temperature of the receptacle to a refrigerated temperature range between about 15 degrees Celsius and a freezing temperature of the platelet concentrate; and
operating an agitation unit to rotate the receptacle while the temperature of the receptacle is within the refrigerated temperature range.

25. The method of claim 24, wherein the agitation unit is configured to rotate the receptacle about a longitudinal axis of the receptacle.

26. The method of claim 24, wherein the control system is configured to control a rate of rotation of the receptacle to maintain the platelet concentrate in a suspended state.

27. The method as defined in claim 24, wherein said receptacle includes a secondary bag said secondary bag including a sealable secondary bag cavity that at least partially contains said storage bag, said storage bag being permeable to a gas system, said secondary bag being impermeable to said gas system when said storage bag is sealed in said secondary bag cavity of said secondary bag.

28. The method as defined in claim 27, wherein said secondary bag is at least partially formed of a flexible material.

29. The method as defined in claim 27, wherein said secondary bag is impermeable to xenon and air when said storage bag is sealed in said secondary bag cavity, and said storage bag is permeable to xenon.

30. The method as defined in claim 29, wherein said secondary bag is formed of a material that includes a coating, a film, or combinations thereof that is impermeable to xenon and air, said storage bag at least partially formed of a material that enables said storage bag to be permeable to xenon.

31. The method as defined in claim 27, wherein said secondary bag is a disposable plastic bag that is configured to be disposed of after said storage bag is removed from said secondary bag cavity.

32. The method as defined in claim 27, wherein said secondary bag includes a gas inlet configured to enable said gas system to be inserted into said secondary bag cavity while said storage bag is at least partially inserted in said secondary bag cavity, said gas inlet configured to be sealable to prevent said gas system in said secondary bag cavity from exiting said secondary bag cavity via said gas inlet.

33. The method as defined in claim 27, wherein said secondary bag includes an adhesive seal, heat seal, or combinations thereof to at least partially seal said storage bag in said secondary bag cavity.

34. The method as defined in claim 27, wherein said secondary bag cavity includes said gas system.

35. The method as defined in claim 34, wherein said secondary bag cavity is filled with said gas system to a pressure no more than 4 bars above ambient pressure.

\* \* \* \* \*